US00PP15103P3

(12) United States Plant Patent
Hancock

(10) Patent No.: US PP15,103 P2
(45) Date of Patent: Aug. 24, 2004

(54) BLUEBERRY PLANT DENOMINATED 'DRAPER'

(50) Latin Name: *Vaccinium corymbosum*
Varietal Denomination: Draper

(75) Inventor: James F. Hancock, East Lansing, MI (US)

(73) Assignee: Board of Trustees operating Michigan State University, East Lansing, MI (US)

( * ) Notice: Subject to any disclaimer, the term of this patent is extended or adjusted under 35 U.S.C. 154(b) by 0 days.

(21) Appl. No.: 10/350,344

(22) Filed: Jan. 23, 2003

(65) Prior Publication Data

US 2004/0148670 P1 Jul. 29, 2004

(51) Int. Cl.[7] ..... A01H 5/00
(52) U.S. Cl. ..... Plt./157

(58) Field of Search ..... Plt./157

*Primary Examiner*—Anne Marie Grunberg
*Assistant Examiner*—S B McCormick-Ewoldt
(74) *Attorney, Agent, or Firm*—Harness, Dickey & Pierce, P.L.C.

(57) ABSTRACT

Draper is a new blueberry variety of *Vaccinium corymbosum* from the Michigan State University breeding program. It is composed primarily of genes of *Vaccinium corymbosum,* but has a small contribution (<5%) from *V. tenellum, V. ashei* and *V. darrowi.* It is a productive, early mid-season ripening variety with very high fresh market quality and probably a long storage life. It is intended for areas where northern highbush cultivars are grown successfully. Plants of Draper are vigorous and upright. Canes are numerous, moderately branched and the fruit are well exposed. Its berries are moderately large, have small, dry picking scars, excellent powder-blue color, delicious flavor and excellent firmness. The size of the fruit is unusually regular and is presented in a loose cluster.

2 Drawing Sheets

Latin name and variety denomination: The present invention relates to a new and distinct variety of *Vaccinium corymbosum,* which is hereby denominated 'Draper.'

CROSS-REFERENCE TO RELATED APPLICATIONS

This application is related to the present inventor's United States patent applications entitled "Blueberry plant denominated 'Aurora,'" U.S. Plant patent application Ser. No. 10/350,345, filed Jan. 23, 2003, and entitled "Blueberry Plant denominated 'Liberty,'" U.S. Plant patent application Ser. No. 10/350,343, filed Jan. 23, 2003. Both of these applications are also assigned to the assignee of the present application. The disclosures of the above applications are hereby incorporated herein by reference.

SUMMARY OF THE INVENTION

The present invention relates to a new and distinct variety of highbush blueberry plant, denominated 'Draper.' Draper is a new blueberry variety of *Vaccinium corymbosum* from the Michigan State University Breeding Program. It includes genes of *Vaccinium corymbosum,* with small contributions of genes from *V. tenellum, V. ashei* and *V. darrowi.* It is a productive, early mid-season ripening variety with very high fresh market quality and is believed to have a long storage life. It is intended for areas where northern highbush varieties are grown successfully. Plants of Draper are vigorous and upright. Canes are numerous, moderately branched and the fruit are well exposed. Its berries are moderately large, have small, dry picking scars, excellent powder-blue color, delicious flavor and excellent firmness. The size of the fruit is unusually regular and is presented in a loose cluster.

Emasculated flowers of the 'Duke' highbush blueberry were pollinated in 1990 with pollen from the USDA elite selection G751. Duke was crossed with G751 to transfer the unusually firm, long-lasting fruit of G751 into the earlier season background of Duke. The seeds were germinated, grown in a greenhouse for 1 year and then field planted at Benton Harbor Mich. Draper was selected in 1995 from 77 siblings. Asexual reproduction took place at East Lansing, Mich. and Lowell, Oreg. The original selection has been evaluated at Benton Harbor annually for 11 years. Draper has been propagated by hardwood cuttings that produced over a hundred shoots which were rooted in the greenhouse and then planted in the field. Initiation of root development from hardwood cuttings takes about two to about four weeks. In addition, Draper has been propagated by softwood cuttings that have been rooted. Furthermore, generation of micro-shoots in the greenhouse using established tissue culture methods has produced thousands of clones of Draper. Initiation of root development from microshoots takes about three to about four weeks. Such methods are discussed in the following references, which are incorporated by reference in their entirety: Doran, W. L. and Bailey, J. S. "Propagation of the high bush blueberry by softwood cuttings," Bulletin Massachusetts Agricultural Experiment Station; no. 410. Amherst, Mass. Massachusetts State College, 1943; Doehlert, C. A. "Propagating blueberries from hardwood cuttings," Circular (New Jersey Agricultural Experiment Station) 490. New Brunswick, N.J. New Jersey Agricultural Experiment Station, 1945; Doehlert, C. A. "Propagating blueberries from hardwood cuttings," Circular (New Jersey Agricultural Experiment Station) 551. New Brunswick, N.J.: New Jersey Agricultural Experiment Station, 1953; El Shiekh, A.; Wildung, D. K.; Luby, J. J.; Sargent, K. L.; Read, P. E. "Long term effects of propagation by tissue culture or softwood single node cuttings on growth habit, yield, and berry weight of 'Northblue' blueberry," Journal of the American Society for Horticultural Science. 1996; 121: 2, 339 342; Galletta, G. J.; Ballington, J. R.; Daubeny, H. A.; Brennan, R. M.; Reisch, B. J.; Pratt, C.; Ferguson, A. R.; Seal, A. G.; McNeilage, M. A.; Fraser, L. G.; Harvey, C. F.; Beatson, R. A.; Hancock, J. F.; Scott, D. H.; Lawrence, F. J.; Janick, J. (ed.); Moore, J. N. "Fruit breeding. Volume II. Vine and small fruits," Department of Horticulture, Purdue University, West Lafayette, Ind. 1996 John Wiley and Sons; New York; USA; Strik, B.; Brun, C.; Ahmedullah, M.; Antonelli, A.; Askham, L.; Barney, D.; Bristow, P.; Fisher, G.; Hart, J.; Havens, D. Draper A. D. and Chandler C. K. "Accelerating highbush blueberry selection evaluation by early propagation," Journal of the American Society for Horticultural Science. 1986 111(2): 301–303; Pritts M. P. and Hancock J. F. (Eds.) "Highbush blueberry production guide," Northeast Regional Agricultural Engineering Service, Ithaca, N.Y., USA 1992.

Clones of Draper have been tested for four years at Benton Harbor, Mich. and Grand Junction, Mich., and for two years at South Haven, Mich., Lacota, Mich., Corvallis, Oreg., and Lowell, Oreg. In all cases all resulting plants have stably displayed characteristics of the variety identified as Draper.

The predominant mid-season blueberry variety now grown, 'Bluecrop,' has very high yields, but the fruit are often sour, do not ripen evenly and have limited storage life. Draper ripens much more regularly, has much better flavor and will store longer. The firmness of its fruit suggests that it can be machine harvested for the fresh market, a characteristic only occasionally possible with Bluecrop. Draper appears to be five days earlier ripening than Bluecrop, partially filling a production void after the major early ripening variety 'Duke.'

Consistent high yields at Benton Harbor and Grand Junction, Mich. indicate that the buds and wood of Draper are tolerant to fluctuating late fall and spring temperatures. Draper also has excellent winter hardiness, as it has routinely been challenged with mid-winter temperatures below −20 C. Probable areas of adaptation and markets include blueberry growers in Michigan and across the USA, Canada, Argentina, Australia, Chile, France, Germany, and New Zealand.

BRIEF DESCRIPTION OF THE DRAWINGS

The present invention will become more fully understood from the detailed description and the accompanying drawings, wherein.

DETAILED BOTANICAL DESCRIPTION

Figure 1:
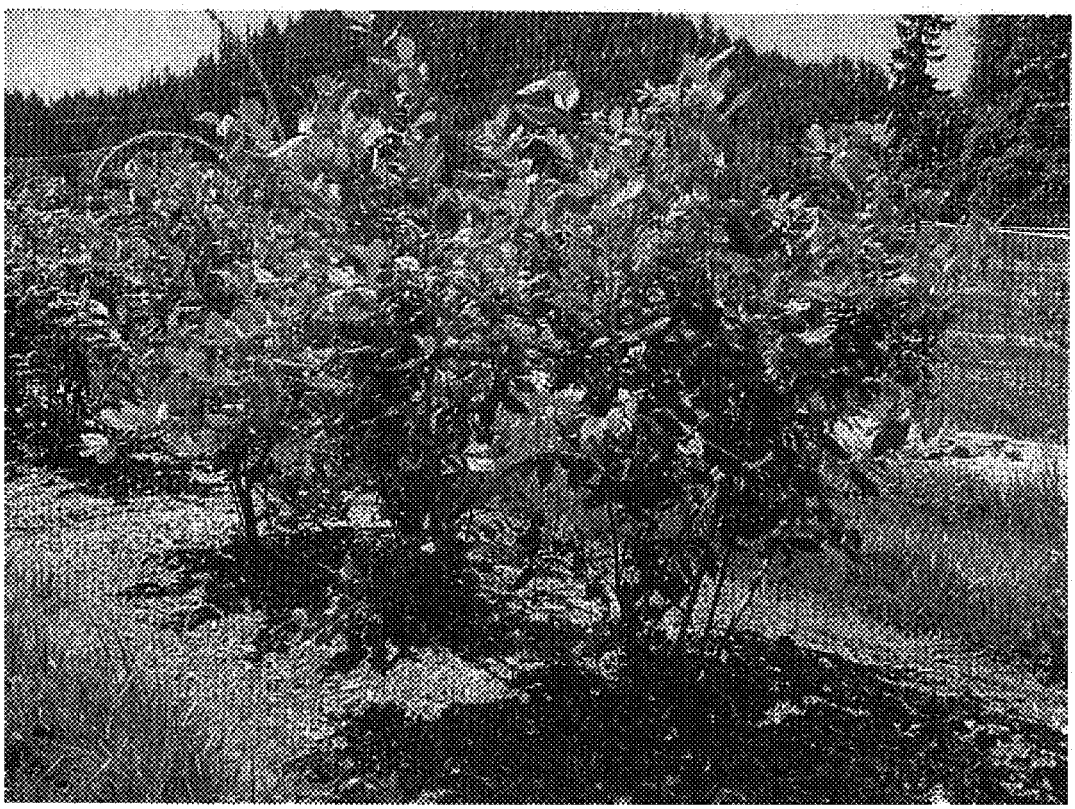
FIG. 1 is a photographic print in full color of three exemplary 4-year-old Draper blueberry plants in a planted row in the foreground. Additional plants or portions thereof in the far left corner, in the background, and the grass on the ground are not part of the Draper blueberry plants.
Figure 2:
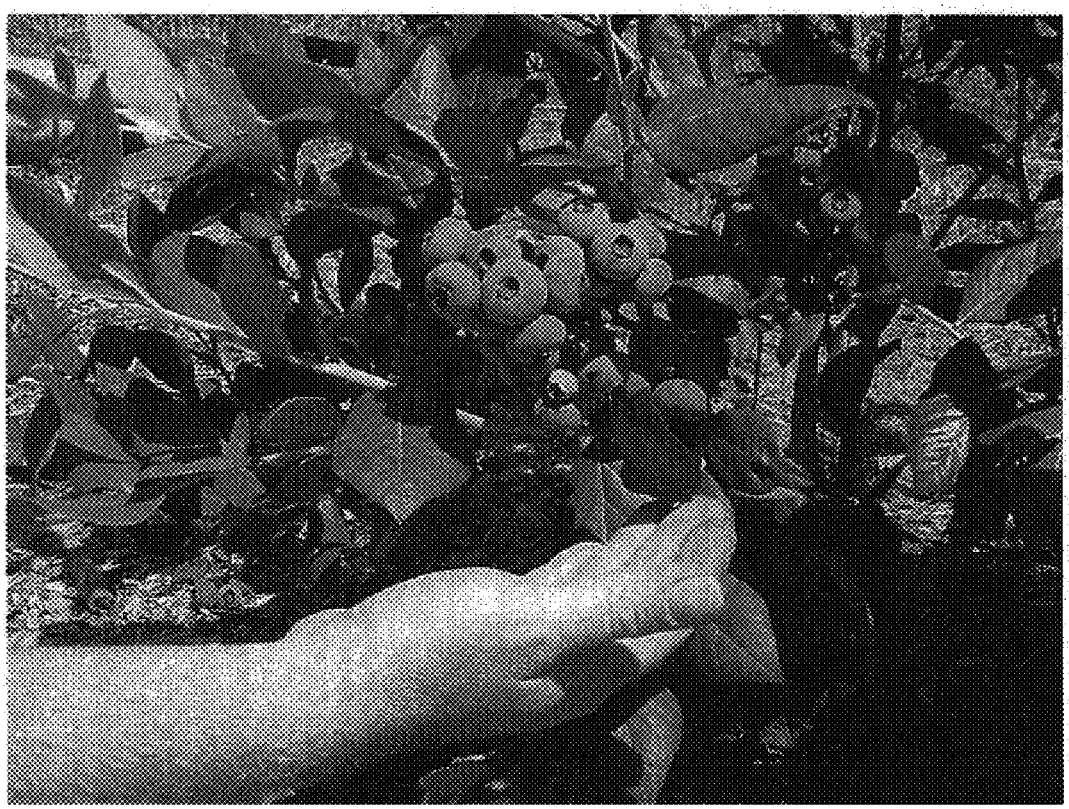
FIG. 2 is a photographic print in full color illustrating exemplary fruit clusters of a 4-year old Draper blueberry plant. Most, but not all, of the fruit shown is mature.

The following is a detailed botanical description of the new and distinct variety of blueberry, its flowers, fruit and foliage, based on observations of specimens grown at Benton Harbor Mich. and Grand Junction, Mich. over four years, and at South Haven, Mich., Lacota, Mich., Corvallis, Oreg., and Lowell, Oreg., over a two year period. The taxonomic characteristics chosen in the detailed description are standard in the practice (R E Gough, R J Hindle, and V G Shutak, "Identification of Ten Highbush Blueberry Cultivars using Morphological Characteristics," *HortScience* 11 (5): 512–4, 1976). Color descriptions, except those given in common terms, are presented in The Royal Horticultural Society Colour Chart designations. In cases where the color descriptions cited from The Royal Horticultural Society Colour Chart differ from the colors shown in the drawings, the colors cited from The Royal Horticultural Society Colour Chart should be considered accurate. Any deviation from these colors in the drawings is due to failure of the photographic process to exactly duplicate the colors of nature. In addition, fruit color designations in Table I are applicable only to mature fruit.

Draper requires pollination for fruit development; it is self-fertile but pollen from any highbush blueberry species will initiate fruit development.

TABLE I

Draper Characteristics

| Characteristic | Draper |
|---|---|
| Bush | |
| Mature height | 1.5 m |
| Mature width | 1.0 m |
| Diameter/width ratio | 2.2 |
| Growth habit | Upright |
| Annual renewal canes | 2–3 |
| Internode length on spring shoots | 2 cm |
| Mature cane color | Greyed-Green (197A) |
| Mature cane length | 1.8 m–2.1 m |
| Mature cane wigth | 2 cm–4 cm |
| Fall color-new shoots | Solid Red-Purple (60A) |
| Foliage | |
| Leaf shape | Narrow elliptic |
| Apex shape | Acute |
| Base shape | Cuniate |
| Leaf length | 2.5 cm–3.5 cm |
| Leaf width | 1.1 cm–1.5 cm |
| Leaf length/width | 1.8 |
| Leaf serration | Entire |
| Pubescence | None |
| Color-top | Green (137C) |
| Color-bottom | Green (138C) |
| Petiole length | 4.5 mm |
| Blossoms | |
| Shape of corolla | Elongate-urceolata |
| Calyx | 5 lobed |
| Style length | At edge of corolla |
| Color of open flower | Mostly white |
| Flower # per cluster | 5–6 |
| Flower diameter | 5 mm–7 mm |
| Reproductive Organs | |
| Type | Berries with seeds |
| Seed size | 1 mm × 2 mm |
| Number of seeds | 10–50 per fruit |
| Mature Fruit | |
| Length | 1.1 cm–1.4 cm |
| Width | 1.5 cm–1.9 cm |
| Color | 156D |
| Shape | Globose, uniform |
| Color with bloom | Violet Blue (98D) |
| Color without bloom | Blue (103A) |
| Pedicel scar size | 1.4 mm |
| Pedicel length | 3 mm–6 mm |
| Pedicel color | Green (143B) |
| Average weight | 1.6 gm |

In four years of trials in Michigan and two in Oregon, the fruit of Draper have been consistently much firmer than Duke and Bluecrop, and have been much better flavored (Tables II and III). Its fruit load has been about equivalent to Duke and slightly lower than Bluecrop. In a postharvest trial conducted in 2002, Draper proved much more resistant to fruit rots than 'Bluecrop', and its fruit remained sound for a much longer time (Table IV). The fruit are eaten fresh, frozen or processed into products like jams, jellies, and yogurt.

Draper is distinguishable from Liberty (co-pending application Ser. No. 10/350,343, filed Jan. 23, 2003) in that Draper is harvested 6–7 weeks before Liberty (late June to early July vs. Mid-August in Michigan). Draper has a bush height/width ratio of about 2.2, while Liberty's is about 1.4. Draper leaves are narrow elliptic (leaf/length ratio is <2), while Liberty's are elliptic-ovate (leaf/length ratio is >2) draper leaves are entire, while Liberty leaves are serrated.

Draper is distinguishable from Aurora (co-pending application Ser. No. 10/350,345, filed Jan. 23, 2003) in that Draper is harvested 7–8 weeks before Aurora (late June to early July vs. late August to early September in Michigan) Draper has a bush height/width ratio of about 2,.2, while Aurora's is about 1.1. Draper leaves are narrow elliptic (leaf/length ratio is <2), while Aurora's are elliptic-ovate (leaf/length ratio is >2).

TABLE II

Characteristics of 'Draper' as compared to 'Duke' and 'Bluecrop' at Grand Junction, MI from 1998 to 2002. Two-year-old plants were set in 1997 at 4 × 10' spacing with 20 other selections. Mean values are presented along with ranges in parenthesis. The rating scale was 1–9, with 1–4 = inferior, 5–6 = acceptable, 7 = good, 8 = very good and 9 = superior.

| Traits | Duke | Draper | Bluecrop |
|---|---|---|---|
| Horticultural | | | |
| Date of first harvest | 6/24 (6/10–6/30) | 7/5 (6/25–7/15) | 7/10 (6/30–7/25) |
| Fruit load | 7 (7–8) | 7 (7–9) | 8 (8–9) |
| Size | 7 (7–8) | 7 (7–8) | 7 (8–9) |
| Color | 7 (7–8) | 8 (8–9) | 8 (7–8) |
| Picking scar | 8 (7–9) | 8 (8–9) | 7 (7–8) |
| Firmness | 8 (7–9) | 9 (8–9) | 7 (7–8) |
| Flavor | 6 (5–7) | 8 (8–9) | 5 (4–6) |
| Taxonomy | | | |
| Leaf pubescence | Glabrous | Glabrous | Pubescent |
| Leaf nectaries | Pronounced | Pronounced | Obscure |
| Leaf shape | Elliptic-oval | Narrow elliptic | Elliptic |
| Leaf length/width ratio | >2 | <2 | >2 |
| Bush diameter/width ratio | 1.5 (1.4–1.6) | 2.2 (2.0–2.4) | 0.8 (0.65–0.90) |

TABLE II-continued

Characteristics of 'Draper' as compared to 'Duke' and 'Bluecrop' at Grand Junction, MI from 1998 to 2002. Two-year-old plants were set in 1997 at 4 × 10' spacing with 20 other selections. Mean values are presented along with ranges in parenthesis. The rating scale was 1–9, with 1–4 = inferior, 5–6 = acceptable, 7 = good, 8 = very good and 9 = superior.

| Traits | Duke | Draper | Bluecrop |
|---|---|---|---|
| Bark texture-young wood | Smooth to rough | All smooth | Smooth to rough |

TABLE III

Mean fruit ratings of 'Draper' and 'Bluecrop' at Lowell and Corvallis, OR in 2002. Two-year-old plants were set in 2000 at 4 × 10' spacing with 26 other selections. Evalutions were made when the bushes were 50% ripe.

| Location | Cultivar | Fruit load | Size | Color | Piking scar | Firm-ness | Flavor |
|---|---|---|---|---|---|---|---|
| Corvallis | Draper | 8[z] | 7 | 8 | 8 | 9 | 8 |
| | Bluecrop | 8 | 7 | 7 | 7 | 7 | 6 |
| Lowell | Draper | 8 | 7 | 8 | 8 | 9 | 8 |
| | Bluecrop | 8 | 7 | 7 | 7 | 7 | 6 |

[z]The rating scale 1–9, with 1–4 = inferior, 5–6 = acceptable, 7 = good, 8 = very good and 9 = superior.

TABLE IV

Postharvest storage life and fungal rots of 'Draper' and 'Bluecrop' harvest at Grand Junction, MI. in 2002. Fruit were picked on the same day, when the bushes were 30–40% ripe.

| Determinations | Bluecrop | Draper |
|---|---|---|
| % of fruit rotted[y] | | |
| Alternaria | 28 | 2 |
| Colletotricum | 31 | 1 |
| Botrytis | 2 | 2 |
| Postharvest life[z] | | |
| % firm fruit after 6 days | 82 | 99 |
| % firm fruit after 11 days | 60 | 86 |
| % firm fruit after 17 days | 10 | 75 |

[y]Fifty fruit were randomly selected from 4 pints and evaluated after being held for ten days at room temperature.
[z]Four pints of fruit were evaluated after being held at 2 C in plastic ziplock bags. Firm fruit were greater than 130 g $mm^{-1}$ using a portable firmness meter.

What is claimed is:

1. A new and distinct highbush blueberry plant, substantially as illustrated and described herein.

* * * * *

UNITED STATES PATENT AND TRADEMARK OFFICE

CERTIFICATE OF CORRECTION

PATENT NO. : PP15,103 P2
DATED : August 24, 2004
INVENTOR(S) : James F. Hancock

It is certified that error appears in the above-identified patent and that said Letters Patent is hereby corrected as shown below:

Column 3,
Line 12, “Havens, D.” should be -- Havens, D., --.

Column 4,
Line 32, “wigth” should be -- width --.

Column 5,
Line 18, “draper” should be -- Draper --.
Line 22, “Michigan)” should be -- Michigan). --.
Line 23, “2,.2” should be -- 2.2 --.

Column 6,
Line 15, “Piking” should be -- Picking --.
Line 25, “harvest” should be -- harvested --.

Signed and Sealed this

First Day of February, 2005

JON W. DUDAS
*Director of the United States Patent and Trademark Office*